United States Patent [19]

Fancher et al.

[11] 4,117,043
[45] Sep. 26, 1978

[54] PROCESS FOR THE MANUFACTURE OF N-(BETA-DIORGANODITHIOPHOSPHORYLETHYL) ARYL AND ALKYL SULFONAMIDES

[75] Inventors: Llewellyn W. Fancher, Orinda; Jeffrey D. Robbins, Berkeley, both of Calif.

[73] Assignee: Stauffer Chemical Company, Westport, Conn.

[21] Appl. No.: 836,322

[22] Filed: Sep. 26, 1977

[51] Int. Cl.$^2$ .................... C07F 9/165; C07F 9/32; C07F 9/40
[52] U.S. Cl. ................................. 260/938; 260/944
[58] Field of Search ........................ 260/978, 944

[56] References Cited

U.S. PATENT DOCUMENTS

| | | | |
|---|---|---|---|
| 3,133,950 | 5/1964 | Pizzarello et al. | 260/458 |
| 3,194,826 | 7/1965 | Goldstein et al. | 260/458 |
| 3,205,253 | 9/1965 | Fancher et al. | 260/944 |
| 3,368,001 | 2/1968 | Szabo et al. | 260/944 |
| 3,392,215 | 7/1968 | Simmone et al. | 260/978 |
| 3,415,909 | 10/1968 | Simmone et al. | 260/979 |

OTHER PUBLICATIONS

Wagner et al, "Synthetic Organic Chemistry," (1953), J. Wiley & Sons, Inc., New York, pp. 822–823.
Noller, "Structure and Properties of Organic Compounds," (1962), W. B. Saunders Co., Philadelphia, Pa., p. 143.

Primary Examiner—Anton H. Sutto
Attorney, Agent, or Firm—M. Henry Heines

[57] ABSTRACT

N-(beta-diorganodithiophosphorylethyl) aryl and alkyl sulfonamides are prepared by a process comprising reacting a compound having the formula $R^1SO_2X$ with 2-aminoethyl hydrogen sulfate and an aqueous solution of $M^1OH$, and reacting the resulting product with a compound having the formula

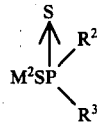

In the above description, $R^1$ is selected from the group consisting of $C_1$–$C_{10}$ alkyl, halo-substituted $C_1$–$C_{10}$ alkyl, phenyl, halo-substituted phenyl, nitro-substituted phenyl, and naphthyl; $R^2$ and $R^3$ are independently selected from the group consisting of $C_1$–$C_{10}$ alkyl and $C_1$–$C_{10}$ alkoxy; X is selected from the group consisting of chloride, bromide, and iodide; and $M^1$ and $M^2$ are independently selected from the group consisting of lithium, sodium, potassium, ammonium, and tri-substituted ammonium wherein the substituents are independently $C_1$–$C_{10}$ alkyl.

15 Claims, No Drawings

PROCESS FOR THE MANUFACTURE OF N-(BETA-DIORGANODITHIOPHOSPHORYLETHYL) ARYL AND ALKYL SULFONAMIDES

BACKGROUND OF THE INVENTION

N-(beta-diorganodithiophosphorylethyl) aryl and alkyl sulfonamides are known for their utility in agricultural applications. For example, U.S. Pat. No. 3,205,253 discloses certain types of these compounds as selective herbicides, and U.S. Pat. No. 3,368,001 discloses other types of these compounds as insecticides and fungicides.

Each of the above-mentioned patents teaches the preparation of the sulfonamides disclosed therein by reaction of a N-(beta-haloalkyl)-aryl or -alkyl sulfonamide with a salt of the appropriate phosphorus compound, such as ammonium diethyldithiophoshate. U.S. Pat. No. 3,415,909 discloses an improvement in the process, whereby the same reaction is carried out at a pH in excess of about 9.5. The N-(beta-haloalkyl)-aryl or -alkyl sulfonamide in these processes is a compound which is prepared by a series of complex batch-wise operations, including a necessary dehydration at several points in the procedure.

Some of these problems were avoided by the discovery of a process involving substituted-sulfonyl ethyleneimines. This process is described in U.S. Pat. No. 3,392,215. The ethyleneimines were reacted directly with a dithiophosphoric acid rather than the acid salt.

It has now been discovered that the use of ethyleneimines can be avoided, as well as the complexity inherent in the preparation of N-(beta-haloalkyl)-aryl or -alkyl sulfonamides. This discovery entails a novel process for the manufacture of N-(beta-diorganodithiophosphorylethyl) aryl and alkyl sulfonamides. This novel process is the process of the present invention, and is fully described hereinbelow.

BRIEF DESCRIPTION OF THE INVENTION

This invention relates to a process for the manufacture of a compound having the formula

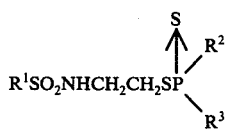

in which $R^1$ is selected from the group consisting of $C_1$–$C_{10}$ alkyl, halo-substituted $C_1$–$C_{10}$ alkyl, phenyl, halo-substituted phenyl, $C_1$–$C_5$ alkyl-substituted phenyl, nitro-substituted phenyl, and naphthyl; and $R^2$ and $R^3$ are independently selected from the group consisting of $C_1$–$C_{10}$ alkyl and $C_1$–$C_{10}$ alkoxy; which comprises (a) reacting a compound having the formula $R^1SO_2X$, in which X is selected from the group consisting of chloride, bromide, and iodide, with 2-aminoethyl hydrogen sulfate and an aqueous solution of a compound having the formula $M^1OH$, in which $M^1$ is selected from the group consisting of lithium, sodium, potassium, ammonium, and tri-substituted ammonium wherein the substituents are independently $C_1$–$C_{10}$ alkyl; and (b) reacting the product of step (a) with a compound having the formula

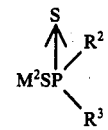

in which $M^2$ is selected from the group consisting of lithium, sodium, potassium, ammonium, and tri-substituted ammonium wherein the substituents are independently $C_1$–$C_{10}$ alkyl, at a pH of at least about 9.5.

DETAILED DESCRIPTION OF THE INVENTION

In its broadest aspect, the process of the invention can be represented by the following equations:

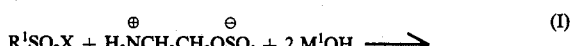

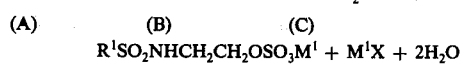

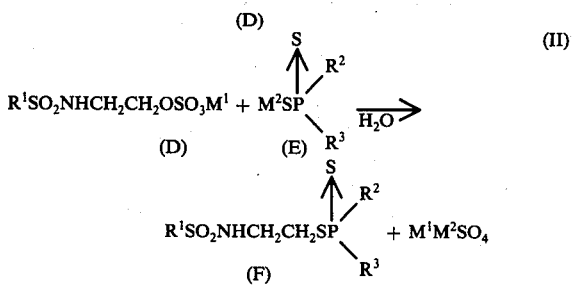

In the above formulas, $R^1$ is selected from the group consisting of $C_1$–$C_{10}$ alkyl, halo-substituted $C_1$–$C_{10}$ alkyl, phenyl, halo-substituted phenyl, $C_1$–$C_5$ alkyl-substituted phenyl, nitro-substituted phenyl, and naphthyl. Preferably, $R^1$ is selected from the group consisting of phenyl, halo-substituted phenyl, $C_1$–$C_5$ alkyl-substituted phenyl, and nitro-substituted phenyl. Most preferably $R^1$ is phenyl. The symbols $R^2$ and $R^3$ represent radicals independently selected from the group consisting of $C_1$–$C_{10}$ alkyl and $C_1$–$C_{10}$ alkoxy. Preferably, $R^2$ and $R^3$ are independently $C_1$–$C_{10}$ alkoxy, and most preferably $C_1$–$C_5$ alkoxy.

The symbol $M^1$ represents a cation selected from the group consisting of lithium, sodium, potassium, ammonium, and tri-substituted ammonium wherein the substituents are independently $C_1$–$C_{10}$ alkyl. Preferably, $M^1$ is selected from the group consisting of sodium and potassium.

The symbol $M^2$ represents a cation selected from the group consisting of lithium, sodium, potassium, ammonium and tri-substituted ammonium wherein the substituents are independently $C_1$–$C_{10}$ alkyl. Preferably, $M^2$ is selected from the group consisting of sodium and potassium.

The symbol X represents a halogen selected from the group consisting of chlorine, bromine, and iodine. Preferably, X is chlorine.

The term "halo" as used in the definition of $R^1$ above is intended to represent fluorine, chlorine, bromine, or iodine, preferably chlorine or bromine. The terms "alkyl" and "alkoxy" are intended to include both straight-chain and branched-chain radicals. All carbon atom ranges are intended to be inclusive of their stated upper and lower limits.

All starting materials shown in Equations (I) and (II) are commercially available. Compound (B), 2-aminoethyl hydrogen sulfate, can be easily prepared from ethanolamine and sulfuric acid. Variations of the basic ethanolamine-sulfuric acid reaction are known in the art, notably the use of a cationic surface-active agent (U.S. Pat. No. 3,133,950), and the removal of water from the reaction mixture by vacuum distillation (U.S. Pat. No. 3,194,826). Both of these references are incorporated herein by reference.

Both reactions are conducted in aqueous solution. Since compound (A) has low solubility in water, it frequently forms a second liquid phase or remains as an undissolved solid until reacted. When either of the latter occur, the progress of Reaction (I) can be greatly enhanced by rapid stirring.

Reaction (I) can be conducted over a broad temperature range, with no particular range being critical to the operation of the reaction. Reactant (A) and product (D) are susceptible to hydrolysis, however, an undesirable side reaction which increases in significance as the system temperature is raised. Hydrolysis will thus be considered along with other factors in determining the preferred operating temperature. Such other factors include the desirability of maintaining a reasonable reaction rate and keeping all components in solution. A convenient operating temperature range is that from about 0° to about 40° C. It will be apparent to one skilled in the art, however, that the appropriate operating temperature will vary, depending on the particular needs of the manufacturing operation where the instant process is used.

In addition to temperature, a high pH tends to increase the incidence of hydrolysis of either reactant (a) or product (D), although no particular pH range is critical to the operability of the reaction. However, improved control of pH and hence hydrolysis can be achieved by conducting the Reaction (I) according to the following three-step procedure:

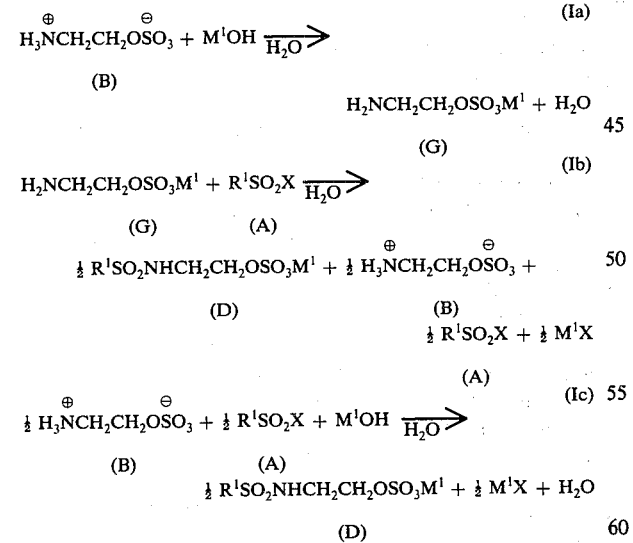

In Reaction (Ia) above, reactant $M^1OH$ is used in the form of an aqueous solution. The molar quantity of $M^1OH$ fed is approximately equal to or less than the molar quantity of reactant (B), in order to minimize hydrolysis of the intermediate (G) and also of reactant (A) which is added in the next step. Although the order of addition in Reaction (Ia) is not critical, it will be most convenient to add the hydroxide to reactant (B) at a rate slow enough to maintain the system temperature within the desired range.

In Reaction (Ib), the ratio in which the reactants are used is not critical and can be varied over a wide range. However, it will be most convenient to use approximately equimolar amounts of both reactants. Optionally, an excess of reactant (G) can be used to assure complete conversion of reactant (A) since the presence of unreacted (A) in the final product (F) poses separation problems.

In the equation given above for Reaction (Ib), it will be noted that ½ mole of reactant (A) does not react. The same result in terms of the quantities of products (D) and (B) can be achieved in this reaction without the addition of this extra ½ mole. The latter is included in the equation, however, to show that the entire quantity of (A) ultimately consumed is most conveniently added at this point.

In Reaction (Ic), the quantity of $M^1OH$ added is such that the total quantity added in this reaction and Reaction (Ia) is approximately twice the molar quantity of reactant (B) used in Reaction (Ia).

It will be most convenient to conduct Reactions (Ia), (Ib) and (Ic) in consecutive order in the same reaction mixture. This is done by adding reactant (A) to the reaction mixture containing reactant (G) resulting from the reaction between $M^1OH$ and reactant (B), and then adding the remaining quantity of $M^1OH$ while the reaction between (A) and (G) is still in progress, or after all the (G) has reacted. Even when the reactants are added in this sequence however, the reaction mechanism as outlined in Equations (Ia), (Ib), and (Ic) above is speculative to the extent that the products shown represent what is believed to be the most probable course followed.

As stated above, Reactions (Ia), (Ib), and (Ic) are operable over a wide range of pH. While there exists no critical pH range for any of these three reactions, some of the reaction products tend to hydrolyze at an increasing rate as the pH is increased. This will not be a significant consideration either in Reaction (Ia) since a deficit of the base is used, or in Reaction (Ib) since the system component (G) is a weak base. A greater chance of hydrolysis exists in Reaction (Ic), however, since a strong base is added directly to the mixture and a deficit of the base is not necessarily maintained. For minimum hydrolysis, the pH during this reaction is preferably maintained below about 12.5, most preferably below about 10.0. Such pH control can be readily achieved by controlling the rate of addition of the base to the mixture.

Similarly, Reactions (Ia), (Ib), and (Ic) are operable over a wide range of temperature, with no criticality as to any particular range. The rate of hydrolysis increases with increasing temperature, however, and the exothermic nature of the reactions renders the system temperature a significant consideration. To minimize hydrolysis while still allowing the reaction to proceed at a reasonable rate, it is most convenient to conduct these reactions at a temperature between about 0° and about 40° C.

The intermediate (D) can be separated from the reaction mixture in which it was prepared, and purified prior to its use in Reaction (II). However, it will be most convenient to forgo a separation and instead add the dithiophosphorus compound (E) directly to the reaction mixture.

The relative amounts of reactants in Reaction (II) are not critical. An excess of the phosphorus compound can be used, however, to increase the reaction rate. A convenient excess would be about 2 to about 20% on a molar basis of reaction (E) over reactant (D).

Reaction (II) can operate over a wide temperature range, with no particular range a critical one. One skilled in the art will realize, however, that although the reaction rate increases with increasing temperature, phosphorus compounds tend to decompose at high temperatures. Compounds where $R^2$ and $R^3$ are both alkyl are the most stable, those where one is alkoxy are intermediate, and those where both are alkoxy are the least stable. Thus the most appropriate operating temperature will depend on the materials being used and the particular needs of any given process. In general, Reaction (II) is conveniently run at a temperature between about 40° and about 100° C.

In order for the reaction to proceed, the system pH must be at least about 9.5, preferably within the range of about 9.5 to about 11.5. At the completion of the reaction, one can minimize the extent of conversion of the final product (F) to a corresponding salt by lowering the system pH to between about 7.0 and about 9.0.

The final product can be recovered from the reaction mixture by any conventional technique known in the art. Since the product is soluble in most organic solvents, it is conveniently extracted from the aqueous mixture by the use of an inert solvent insoluble or slightly soluble in water. Examples of such solvents are benzene, cyclohexane, chloroform, methylene chloride, and toluene. The solvent can then be removed by any conventional technique such as, for example, steam stripping, vacuum distillation, or inert gas sparging.

The following examples are offered to illustrate the process of the invention, and are not intended to limit the invention in any manner.

EXAMPLE I

A mixture of 7.3 grams (0.052 mole) of 2-aminoethyl hydrogen sulfate in 25 milliliters of water was cooled to below 10° C. To the mixture was added 8.2 grams (0.103 mole, 5.5 milliliters) of 50% aqueous sodium hydroxide while the temperature of the mixture was maintained below 15° C. The mixture was then stirred at ambient temperature until all solids dissolved. Upon recooling, the mixture was maintained below 10° C while 8.8 grams (0.05 mole, 6.6 milliliters) of benzenesulfonyl chloride was added. The mixture was stirred in an ice bath for 0.5 hour, then at 25°–30° C for 15 minutes, followed by 40°–45° C for 5 minutes.

During continued stirring, 15.1 grams (0.06 mole) of potassium diisopropyl dithiophosphate was added to the above mixture. The system pH was adjusted from about 8.0 to about 11.0 by the addition of 50% aqueous sodium hydroxide. The mixture was then stirred and heated at 85°–88° C for 1.5 hours. The mixture was then cooled to 25° C and the pH adjusted to about 8–9 with dilute hydrochloric acid.

Additional water was added to the mixture and the product was extracted with benzene. The benzene solution was washed with dilute sodium chloride solution, dried over magnesium sulfate, filtered, and evaporated to yield 16.7 grams (84% overall yield) of liquid product with refractive index $n_D^{30} = 1.5410$. The product was identified as N-(beta-O,O-diisopropyldithiophosphorylethyl)-benzenesulfonamide by infrared analysis and thin-layer chromatography. The purity of the product as determined by high pressure liquid chromatography was 76.8%.

EXAMPLE II

A nitrogen-filled reactor was charged with 36.7 grams (0.260 mole) of 2-aminoethyl hydrogen sulfate and 125 milliliters of water. The mixture was cooled to 5° C, and 20.8 grams (0.260 mole) of 50% aqueous sodium hydroxide was added at 5°–10° C, while the pH rose from 3.0 to 12.0. The reaction mixture was cooled to 7° C, and 44.2 grams (0.250 mole) of benzenesulfonyl chloride was added at 7°–8° C. The temperature was held at 20°–25° C, and 20.4 grams (0.255 mole) of 50% aqueous sodium hydroxide was added at a rate such that the pH remained between 7 and 10. The final pH was 9.7.

An aqueous solution of 0.30 mole of sodium O,O-diisopropylphosphorodithioate, prepared by reacting 25% aqueous sodium hydroxide with O,O-diisopropylphosphorodithioic acid, was added to the solution of the preceding paragraph at 20° C. Addition of 50% aqueous sodium hydroxide brought the pH from 9.7 to 11.0. The mixture was then heated to 90° C for 2 hours with vigorous stirring, followed by cooling to room temperature and acidification with 12N hydrochloric acid from pH 12.7 to pH 8.

Further water was added and the reaction product was extracted with toluene. The toluene extract was washed with 5% aqueous sodium chloride and dried. The solvent was removed in a rotary evaporator to yield 90.0 grams (90.6% yield) of a clear, brown, viscous oil, identified as N-(beta-O,O-diisopropyldithiophosphorylethyl)-benzenesulfonamide by infrared and nuclear magnetic resonance analysis. The purity of the product as determined by high pressure liquid chromatography was 92.1%.

What is claimed is:

1. A process for the manufacture of a compound having the formula

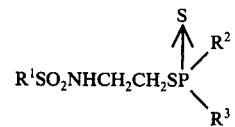

in which $R^1$ is selected from the group consisting of $C_1$–$C_{10}$ alkyl, halo-substituted $C_1$–$C_{10}$ alkyl, phenyl, halo-substituted phenyl, $C_1$–$C_5$ alkyl-substituted phenyl, nitro-substituted phenyl, and naphthyl; and $R^2$ and $R^3$ are independently selected from the group consisting of $C_1$–$C_{10}$ alkyl and $C_1$–$C_{10}$ alkoxy; which comprises (a) reacting 2-aminoethyl hydrogen sulfate with an aqueous solution of a compound having the formula $M^1OH$, in which $M^1$ is selected from the group consisting of lithium, sodium, potassium, ammonium, and tri-substituted ammonium wherein the substituents are independently $C_1$–$C_{10}$ alkyl, at a $M^1OH$: (2-aminoethyl hydrogen sulfate) mole ratio of less than or equal to approximately 1.0;

(b) reacting the product of step (a) with approximately an equimolar amount of a compound having the formula $R^1SO_2X$, in which X is selected from the group consisting of chloride, bromide, or iodide;

(c) reacting the product of step (b) with a further quantity of an aqueous solution of a compound having the formula M¹OH such that the total molar quantity of M¹OH used in this step and step (a) is approximately twice the molar quantity of 2-aminoethyl hydrogen sulfate used in step (a) and the pH is maintained below about 12.5; and (d) reacting the product of step (c) with a compound having the formula

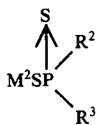

in which $M^2$ is selected from the group consisting of lithium, sodium, potassium, ammonium, and tri-substituted ammonium wherein the substituents are independently $C_1-C_{10}$ alkyl, at a pH of at least about 9.5.

2. A process according to claim 1 in which $R^1$ is selected from the group consisting of phenyl, halo-substituted phenyl, $C_1-C_5$ alkyl-substituted phenyl, and nitro-substituted phenyl.

3. A process according to claim 1 in which $R^2$ and $R^3$ are independently $C_1-C_{10}$ alkoxy.

4. A process according to claim 1 in which $R^2$ and $R^3$ are independently $C_1-C_5$ alkoxy.

5. A process according to claim 1 in which $M^1$ is selected from the group consisting of sodium and potassium.

6. A process according to claim 1 in which $M^2$ is selected from the group consisting of sodium and potassium.

7. A process according to claim 1 in which X is chloride.

8. A process according to claim 1 in which $R^1$ is selected from the group consisting of phenyl, halo-substituted phenyl, $C_1-C_5$ alkyl-substituted phenyl, and nitro-substituted phenyl; $R^2$ and $R^3$ are independently $C_1-C_5$ alkoxy; $M^1$ and $M^2$ are independently selected from the group consisting of sodium and potassium; and X is chloride.

9. A process according to claim 1 in which $R^1$ is phenyl, $R^2$ is isopropoxy, $R^3$ is isopropoxy, $M^1$ is sodium, $M^2$ is sodium, and X is chloride.

10. A process according to claim 1 in which step (a) is conducted at a temperature between about 0° and about 40° C.

11. A process according to claim 1 in which step (b) is conducted at a temperature between about 0° and about 40° C.

12. A process according to claim 1 in which step (c) is conducted at a temperature between about 0° and about 40° C.

13. A process according to claim 1 in which step (d) is conducted at a temperature between about 40° and about 100° C.

14. A process according to claim 1 in which step (d) is conducted at a pH maintained between about 9.5 and about 11.5.

15. A process according to claim 1 in which step (d) is conducted at a pH maintained between about 10.5 and about 11.5.